(12) United States Patent
Nakagawa et al.

(10) Patent No.: US 12,171,928 B2
(45) Date of Patent: Dec. 24, 2024

(54) SUCTION BOTTLE FOR THROMBUS ASPIRATOR AND THROMBUS ASPIRATOR

(71) Applicant: NIPRO CORPORATION, Osaka (JP)

(72) Inventors: Naoki Nakagawa, Osaka (JP); Junichi Muto, Osaka (JP); Kuniaki Matsumoto, Osaka (JP)

(73) Assignee: NIPRO CORPORATION, Osaka (JP)

( * ) Notice: Subject to any disclaimer, the term of this patent is extended or adjusted under 35 U.S.C. 154(b) by 223 days.

(21) Appl. No.: 17/615,717

(22) PCT Filed: Jun. 1, 2020

(86) PCT No.: PCT/JP2020/021642
§ 371 (c)(1),
(2) Date: Dec. 1, 2021

(87) PCT Pub. No.: WO2020/246431
PCT Pub. Date: Dec. 10, 2020

(65) Prior Publication Data
US 2022/0241485 A1 Aug. 4, 2022

(30) Foreign Application Priority Data
Jun. 3, 2019 (JP) .................. 2019-103762

(51) Int. Cl.
*A61M 1/00* (2006.01)
*A61B 10/00* (2006.01)
(Continued)

(52) U.S. Cl.
CPC ........... *A61M 1/60* (2021.05); *A61B 10/0045* (2013.01); *A61B 10/0096* (2013.01); *A61B 10/02* (2013.01);
(Continued)

(58) Field of Classification Search
CPC . A61B 10/0045; A61B 10/0096; A61B 10/02; A61M 1/79; A61M 1/60; A61M 1/0281; A61M 1/3627; A61M 2205/7545
See application file for complete search history.

(56) References Cited

U.S. PATENT DOCUMENTS

2005/0171495 A1* 8/2005 Austin .................... A61M 1/88
604/317
2012/0165642 A1 6/2012 Krensky et al.
(Continued)

FOREIGN PATENT DOCUMENTS

| CN | 205055150 U | 3/2016 |
| JP | 2004-049706 A | 2/2004 |

(Continued)

OTHER PUBLICATIONS

Extended European Search Report in European Application No. 20818698.1, issued Dec. 8, 2022, 8 pages.
(Continued)

*Primary Examiner* — Kai H Weng
(74) *Attorney, Agent, or Firm* — Jason M. Shapiro; Devlin Law Firm LLC (57) ABSTRACT

A suction bottle for a thrombus aspirator is equipped with a thrombus trapping member that spreads so as to separate the inside of the bottle into an upper region and a lower region. The thrombus trapping member is provided with a plurality of through-holes that cause blood guided to the upper surface to flow down from the upper region to the lower region.

12 Claims, 7 Drawing Sheets

(51) Int. Cl.
  *A61B 10/02* (2006.01)
  *A61M 1/02* (2006.01)
  *A61M 1/36* (2006.01)

(52) U.S. Cl.
  CPC ......... *A61M 1/0281* (2013.01); *A61M 1/3627* (2013.01)

(56) References Cited

U.S. PATENT DOCUMENTS

| | | | |
|---|---|---|---|
| 2016/0030486 A1* | 2/2016 | Cimino | A61M 1/892 435/378 |
| 2016/0151550 A1* | 6/2016 | Fisher | A61M 1/63 210/418 |
| 2016/0213355 A1 | 7/2016 | Parks | |
| 2018/0353194 A1 | 12/2018 | Shaffer et al. | |

FOREIGN PATENT DOCUMENTS

| | | |
|---|---|---|
| JP | 2012-500105 A | 1/2012 |
| WO | 2018/031048 A1 | 2/2018 |

OTHER PUBLICATIONS

English Translation of International Preliminary Report on Patentability for International Application No. PCT/JP2020/021642 issued on Dec. 7, 2021 (6 pages).

International Search Report issued in International Patent Application No. PCT/JP2020/021642 mailed Aug. 4, 2020 (4 pages), with English translation.

Office Action in corresponding Japanese Patent Application No. 2021-524836, issued May 7, 2024, with English translation (9 pages).

Office Action in corresponding Japanese Patent Application No. 2021-524836, issued Sep. 19, 2024, with English translation (11 pages).

* cited by examiner

SUCTION BOTTLE FOR THROMBUS ASPIRATOR AND THROMBUS ASPIRATOR

CROSS-REFERENCE TO RELATED APPLICATIONS

This application is a U.S. National Stage of International Application No. PCT/JP2020/021642, filed on Jun. 1, 2020, and claims priority under 35 U.S.C. § 119 to Japanese Application No. JP 2019-103762, filed on Jun. 3, 2019, the contents of which are incorporated by reference herein in their entirety.

TECHNICAL FIELD

The present invention relates to a suction bottle used in a thrombus aspirator for collecting a thrombus wherein the suction bottle is used for accommodating the sucked blood, and a thrombus aspirator assembled with the suction bottle.

BACKGROUND ART

Conventionally, a thrombus aspirator that sucks a thrombus and restores blood flow has been known in order to clear the clogging of a blood vessel due to a thrombus. The present applicant proposes such a medical aspirator in Japanese Unexamined Patent Publication No. JP-A-2004-49706 (Patent Document 1).

The medical aspirator described in Patent Document 1 includes a suction material collection bottle, and the blood sucked together with the thrombus is contained in the suction material collection bottle.

BACKGROUND ART DOCUMENT

Patent Document

Patent Document 1: JP-A-2004-49706

SUMMARY OF THE INVENTION

Problem the Invention Attempts to Solve

By the way, when urgent treatment is required like a cerebral infarction patient, it is necessary to promptly take measures until the blood flow is restored by aspirating the thrombus. Therefore, it is desirable that the practitioner can easily and quickly confirm that the aspirated blood contains a thrombus. Alternatively, the collected thrombus may be inspected precisely, and it is desirable that only the thrombus can be easily separated from the aspirated blood.

The problem to be solved by the present invention is that the practitioner can easily and quickly confirm the presence of a thrombus in the aspirated blood, that the aspirated blood and the thrombus can be easily separated, and that the bottle is compact so that it can be easily handled. It is an object of the present invention to provide a suction bottle or a thrombus aspirator having a novel structure capable of solving at least one of the problems inherent in a conventional suction bottle or a thrombus aspirator.

Means for Solving the Problem

Hereinafter, preferred embodiments for grasping the present invention will be described, but the respective embodiments described below are described by way of example, and not only can be appropriately combined with each other and adopted, but also described in each embodiment. The plurality of components of the above can be recognized and adopted independently as much as possible, and can be appropriately adopted in combination with any of the components described in another embodiment. Thereby, in the present invention, various other aspects can be realized without being limited to the aspects described below.

A first preferred embodiment provides a suction bottle for a thrombus aspirator comprising: a thrombus trapping member that spreads so as to divide an inside of the bottle into an upper region and a lower region; and a plurality of through holes formed in the thrombus trapping member so that blood guided to an upper surface of the thrombus trapping member flows down from the upper region to the lower region via the through holes.

According to the suction bottle of this embodiment, the blood clot containing the thrombus is allowed to flow down the inside of the bottle, so that the thrombus is filtered and captured by the thrombus trapping member. By visually confirming the upper surface of the thrombus trapping member from the outside, it is possible to easily and quickly grasp whether or not the thrombus has been recovered. Further, in this embodiment, the thrombus can be easily separated from the sucked blood. In this embodiment, since the thrombus trapping member spreads so as to divide the inside of the bottle into the upper region and the lower region, it is avoided that blood introduced from above collects at the bottom together with the thrombus as in the case using a mesh bag or the like. In this embodiment, the blood spreads to the upper surface of the thrombus trapping member and quickly flows down, and the thrombus is left on the upper surface of the thrombus trapping member, thereby facilitating visual confirmation. It should be noted that it is not necessary that a plurality of the above effects are exhibited at the same time, and at least one effect may be exhibited.

A second preferred embodiment provides the suction bottle according to the first preferred embodiment, further comprising a ventilation passage that allows a flow of air between the upper region and the lower region inside the bottle, the ventilation passage being provided at a position avoiding an inflow port of the blood in the upper region.

According to the suction bottle of this embodiment, the air in the lower region flows to the upper region through the ventilation passage, so that the blood can flow down smoothly through the through hole. In addition, since the ventilation passage is provided at a position avoiding the blood inlet, it is possible to avoid occurrence of the following problems, namely, the ventilation passage is blocked by blood, or the blood flowing in from the inlet immediately flows down to the lower region through the ventilation passage.

A third preferred embodiment provides the suction bottle according to the second preferred embodiment, wherein the thrombus trapping member includes: a plate-shaped portion extending between the upper region and the lower region; and a tubular portion with a hollow inside that projects upward from the plate-shaped portion, and the ventilation passage is formed by the hollow inside of the tubular portion.

According to the suction bottle of this embodiment, the ventilation passage is formed by the tubular portion protruding upward from the plate-shaped portion. This makes it possible to prevent that the blood introduced into the plate-shaped portion infiltrates into the ventilation passage thereby closing or narrowing the ventilation passage.

A fourth preferred embodiment provides the suction bottle according to any of the first through third preferred embodiments, wherein the thrombus trapping member includes: a plate-shaped portion extending between the upper region and the lower region; and a peripheral vertical wall portion that rises upward at an outer peripheral portion of the plate-shaped portion.

According to the suction bottle of this embodiment, it is possible to prevent the thrombus from flowing down from the outer peripheral side of the plate-shaped portion to the lower region. By using the peripheral vertical wall portion as a reinforcing portion, it is possible to reduce the thickness of the plate-shaped portion and improve the degree of freedom in selecting the material of the plate-shaped portion.

A fifth preferred embodiment provides the suction bottle according to the fourth preferred embodiment, wherein the peripheral vertical wall portion is formed by a cylindrical peripheral wall portion so that the thrombus trapping member is formed into a cup shape as a whole, and the thrombus trapping member is supported with respect to a bottle body at the upper opening portion of the peripheral wall portion.

According to the suction bottle of this embodiment, the ability of the thrombus trapping member to hold the thrombus can be improved by forming the cup shape. Further, the thrombus trapping member of cup shape is supported by the bottle body by using the peripheral wall portion, making it possible to simplify or make compact the structure of the thrombus trapping member and the bottle body.

A six preferred embodiment provides the suction bottle according to the fourth or fifth preferred embodiment when related to third preferred embodiment, wherein the thrombus trapping member can be gripped by fingers by picking the tubular portion provided on the thrombus trapping member.

According to the suction bottle of this embodiment, the thrombus trapping member can be picked and handled by using the tubular portion of the thrombus trapping member. This makes it possible to realize the ventilation passage and a pinching portion with a simple and compact structure.

A seventh preferred embodiment provides the suction bottle according to any one of the first to sixth preferred embodiments, wherein the thrombus trapping member includes a plate-shaped portion extending between the upper region and the lower region, and at least one of the upper surface and a lower surface of the plate-shaped portion has an inclined portion inclined with respect to a horizontal direction.

According to the suction bottle of this embodiment, by providing the plate-shaped portion with an inclination, the blood on the thrombus trapping member or the blood that has circulated to the lower surface of the thrombus trapping member through the through hole is positively directed downward in the inclined direction. This makes it possible to define a flow direction of blood in the plate-shaped portion, Therefore, it becomes easy to confirm the thrombus left in the plate-shaped portion in a mounted state, for example. Alternatively, when the ventilation passage of the second preferred embodiment is employed in combination, for example, the inclined portion is configured to allow the blood to flow in the direction away from the ventilation passage in the plate-shaped portion. This makes it possible to reduce the possibility that the blood wrapping around the lower surface of the thrombus trapping member blocks the ventilation passage, by An eighth preferred embodiment provides the suction bottle according to any one of the first to seventh preferred embodiments, further comprising: a bottle housing of a closed structure for accommodating the thrombus trapping member, the bottle housing having a bottle body that opens upward and a bottle lid that covers an opening of the bottle body, wherein the bottle lid includes: a blood suction port to which a suction tube for sucking the blood into the inside of the bottle is connected; and a negative pressure action port to which a negative pressure tube for applying a suction pressure to the suction tube via the inside of the bottle is connected, the blood suction port and the negative pressure action port being provided at different positions on the bottle lid.

According to the suction bottle of this embodiment, the two ports for external connection provided in the suction bottle can be provided on the bottle lid. Therefore, the structure of the suction bottle can be made compact, and in particular, the shape and structure of the bottle body for storing blood and the like can be easily simplified. Further, for example, it is possible to remove only the bottle body containing the sucked blood or thrombus while the externally connected tube is connected.

A ninth preferred embodiment provides the suction bottle according to any one of the first to eighth preferred embodiments, further comprising: a bottle housing of a closed structure for accommodating the thrombus trapping member, the bottle housing having a bottle body that opens upward and a bottle lid that covers an opening of the bottle body, wherein the thrombus trapping member is supported by a sealing member that seals an assembly portion between the bottle body and the bottle lid, and the sealing member realizes a sealability of the assembled portion between the bottle body and the bottle lid regardless of a presence or absence of the thrombus trapping member.

According to the suction bottle of this embodiment, for example, it is possible to realize the sealability of the bottle housing by suppressing the influence of the presence/absence of the thrombus trapping member, the assembled state, the dimensional error, and the like. Therefore, for example, even when the bottle housing is shared and a plurality of types of thrombus trapping members are selectively adopted, stable sealability of the bottle housing can be realized. Also, for example, even after the thrombus trapping member is removed and the thrombus is sent for inspection or the like, the bottle housing containing the blood can be sealed.

A tenth preferred embodiment provides the suction bottle according to any one of the first to ninth preferred embodiments, wherein the thrombus trapping member is provided with a knob portion protruding to the upper region.

According to the suction bottle of this embodiment, the thrombus trapping member can be handled by picking the gripped portion with a finger, and the thrombus trapping member can be easily attached to and detached from the bottle body, for example. In particular, since the knob portion protrudes to the upper region, it is possible to suppress an adhesion of blood to the gripped portion.

An eleventh preferred embodiment provides a thrombus aspirator comprising: a thrombus aspirator main body provided with a negative pressure pump; a suction bottle according to any one of the first to tenth preferred embodiments, the suction bottle being detachably assembled to the thrombus aspirator main body; and a negative pressure tube communicated with an inside of the suction bottle, the negative pressure tube being detachably connected to a negative pressure port of the negative pressure pump.

According to the thrombus aspirator of this embodiment, it is possible to carry out thrombus aspiration using the suction bottles of various preferred embodiments of the present invention as described above.

A twelfth preferred embodiment provides the thrombus aspirator according to the eleventh preferred embodiment, wherein the thrombus aspirator main body includes a holding portion for holding the suction bottle in a state where a deepest portion of the inside of the suction bottle is located at a position at a height of ½ or more in a height direction of the thrombus aspirator main body.

According to the thrombus aspirator of this embodiment, since the bottom of the suction bottle is set at a relatively high position, for example, the blood collected at the bottom of the suction bottle and the thrombus held in the middle of the suction bottle can be easily visually confirmed. In particular, in the treatment area where a thrombus aspirator is used, many equipments and devices are often installed in a narrow area that is easy for the practitioner to operate. Therefore, in the thrombus aspirator according to this embodiment, it is desirable to set, for example, a switch or a meter of a negative pressure pump on the upper surface of the housing in terms of improving visibility. Additionally, in this embodiment, the suction bottle is held with its bottom highly positioned. This makes it possible to perform good visual confirmation of the sucked blood and the thrombus while ensuring good operability at the time of performing the thrombus suction operation using the thrombus aspirator. The holding portion in this embodiment does not limit the specific structure, and is realized by, for example, providing a surface on which the suction bottle is placed, providing a suspension portion for suspending the suction bottle, and the like.

Effect of the Invention

According to the present invention, the practitioner can easily and quickly confirm the presence of a thrombus in the sucked blood, the sucked blood and the thrombus can be easily separated, and/or the bottle is made compact so as to be easy to handle. Namely, at least one of the problems inherent in conventional suction bottles or thrombus aspirators can be solved by the present invention.

EMBODIMENTS FOR CARRYING OUT THE INVENTION

Hereinafter, in order to clarify the present invention in more detail, practical embodiments of the present invention will be described in detail with reference to the drawings.

Figure 1:
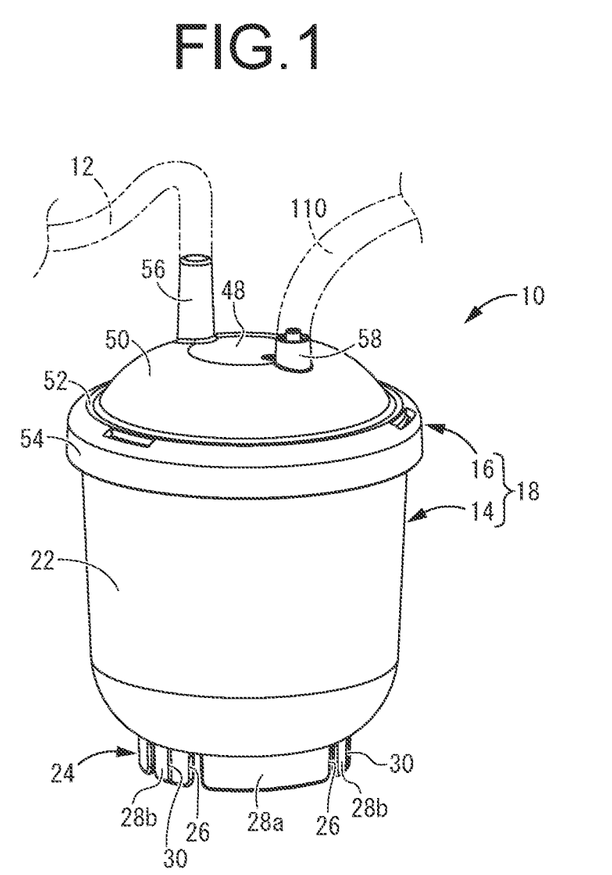
FIG. 1 is a perspective view showing a suction bottle according to a first practical embodiment of the present invention.
Figure 2:
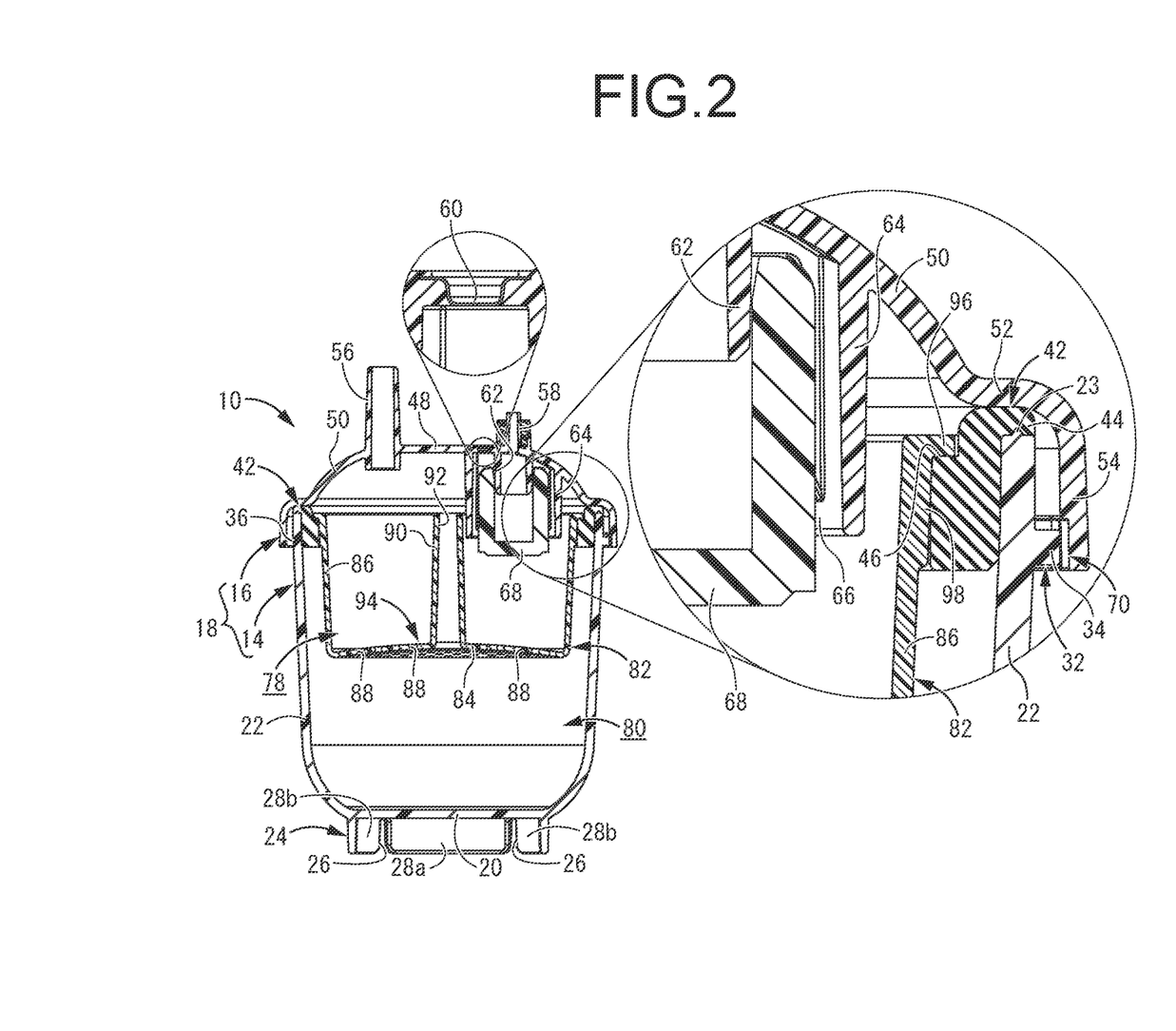
FIG. 2 is a vertical cross sectional view of the suction bottle shown in FIG. 1.

First, FIGS. 1 and 2 show a suction bottle 10 for a thrombus aspirator as a first practical embodiment of the present invention. A suction catheter 12 as a suction tube for thrombus suction is connected to the suction bottle 10. The suction catheter 12 sucks blood in a portion clogged by the thrombus, for example, in a patient with cerebral infarction. A thrombus is collected together with blood in the suction bottle 10. In the following description, the vertical direction refers to the vertical direction in FIG. 2, which is a substantially vertical direction, and the substantially horizontal direction orthogonal to the vertical direction is referred to as a horizontal direction.

More specifically, the suction bottle 10 includes a bottle housing 18 having a sealed structure including a bottle body 14 that opens upward and a bottle lid 16 that covers the opening of the bottle body 14. The bottle housing 18 can be formed of, for example, a hard synthetic resin, and is preferably formed of a transparent (including translucent) material. In the present practical embodiment, substantially the entire bottle housing 18 is transparent materials.

Figure 3:
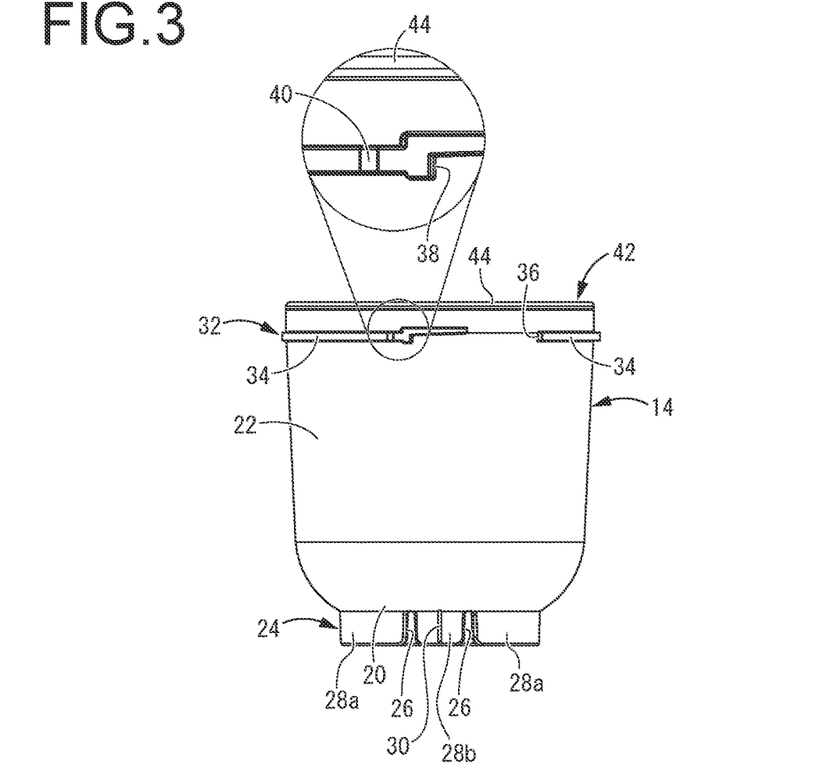
FIG. 3 is a front elevational view of a bottle body of the suction bottle with a state where a sealing member is attached thereto.
Figure 4:
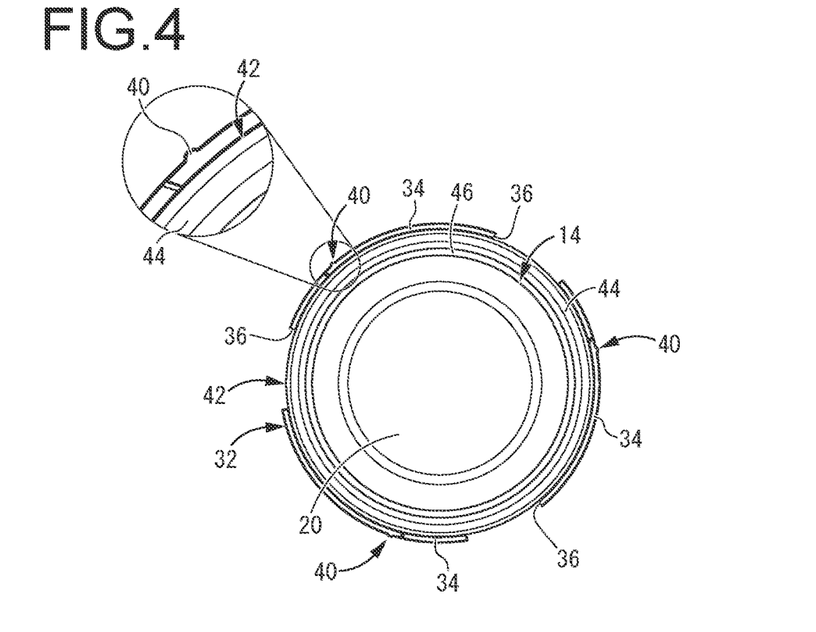
FIG. 4 is a plan view of the bottle body shown in FIG. 3.

In FIGS. 3 and 4, the bottle body 14 is shown in a state where the sealing member 42, which will be described later, is attached. The bottle body 14 has a substantially bottomed cylindrical shape as a whole, and includes a substantially circular bottom wall portion 20 and a cylindrical wall portion 22 projecting upward from the outer peripheral edge portion of the bottom wall portion 20. An annular rib 23 is provided on the upper end surface of the cylindrical wall portion 22 in the radial intermediate portion over the entire circumference in the circumferential direction.

Further, a leg portion 24 projecting downward is provided on the outer peripheral edge portion of the bottom wall portion 20. The leg portion 24 has a substantially constant cross-sectional shape as a whole (the shape of the axial cross section including the central axis of the bottle body 14) and has a substantially cylindrical shape extending over the entire circumference in the circumferential direction. By providing the notch 26, it is composed of a plurality of projecting pieces 28 partially provided in the circumferential direction. In the present practical embodiment, the leg portion 24 is configured to include a long projecting piece 28a having a large circumferential dimension and a short projecting piece 28b having a small circumferential dimension. The three long projecting pieces 28a and the three short projecting piece 28b are provided alternately in turn in the circumferential direction. As a result, the short projectile 28b having a small circumferential dimension can be flexed and deformed in the radial direction (for example, the left-right direction in FIG. 2) relatively easily as compared with the long projectile 28a. In particular, in the present practical embodiment, a fitting protrusion 30 extending in the vertical direction is provided at substantially the center in the circumferential direction on the outer peripheral surface of the short projecting piece 28b.

A body-side engaging portion 32 that engages with the bottle lid 16 is provided at the upper end portion of the outer peripheral surface of the cylindrical wall portion 22. The engagement structure between the bottle body 14 and the bottle lid 16 is not limited, but the body-side engaging portion 32 of the present practical embodiment includes a plurality (three in this practical embodiment) of engaging ridges 34 projecting to the outer peripheral side and partially extending in the circumferential direction, and gaps 36 each provided between the circumferentially adjacent engaging ridges 34, 34. A step is provided at one end of the engaging ridge 34 in the circumferential direction, and a dead end surface 38 formed by the step is provided. Further, on the outer peripheral surface of the engaging ridge 34, a body-side engaging protrusion 40 projecting to the outer peripheral side is provided on the other side in the circumferential direction from the dead end surface 38. In the present practical embodiment, unless otherwise specified, the circumferential direction means a direction of rotation around the central axis of the suction bottle 10 extending in the vertical direction. In particular, in the present practical embodiment, when the suction bottle 10 is viewed from above, the counterclockwise direction is called the one circumferential direction, and the clockwise direction is called the other circumferential direction.

The seal member 42 is attached to the bottle body 14. The sealing member 42 has an annular shape as a whole, and is formed of an elastic body such as rubber or an elastomer. The outer diameter dimension of the sealing member 42 is substantially equal to or slightly larger than the inner diameter dimension at the upper end portion of the cylindrical wall portion 22. Further, an annular flange portion 44 projecting to the outer peripheral side is provided at the upper end of the sealing member 42, and the outer diameter dimension of the flange portion 44 is substantially equal to the outer diameter dimension at the upper end of the cylindrical wall portion 22. As a result, the flange portion 44 is placed on the upper end surface of the cylindrical wall portion 22 and welded or adhered as necessary, so that the sealing member 42 is substantially coaxial with and supported by the bottle body 14 at the upper opening of the bottle body 14. In such a mounting state, it is preferable that the main body portion of the sealing member 42 excluding the flange portion 44 is slightly compressed toward the inner peripheral side by the cylindrical wall portion 22. Further, in the main body portion of the sealing member 42, the upper surface of the inner peripheral portion is an annular surface that extends laterally at a height position lower than the outer peripheral portion having the flange portion 44, and the annular surface provides a support surface 46, described later, that supports the thrombus trapping member 82.

Figure 5:
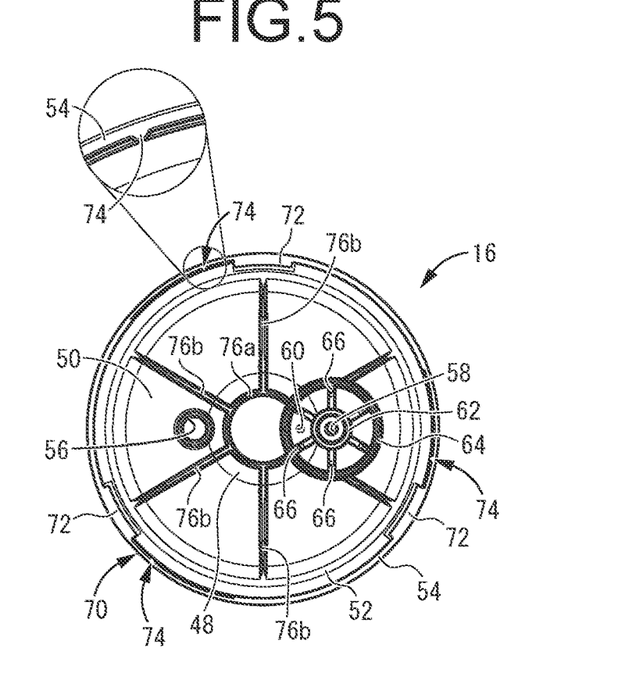
FIG. 5 is a bottom view of a bottle lid of the suction bottle shown in FIG. 1.

The bottle lid 16 has substantially a reversed dish shape as a whole, having a circular upper bottom wall portion 48 in the central portion and an annular wall portion 50 spreading gently downward from the outer peripheral edge portion of the upper bottom wall portion 48. Further, an annular flange-shaped portion 52 extending in the lateral direction is provided on the outer peripheral edge portion of the annular wall portion 50, and a cylindrical portion 54 projecting downward is provided on the outer peripheral edge portion of the flange-shaped portion 52.

The upper bottom wall portion 48 or the annular wall portion 50 is provided with a patient-side port 56 as an inflow port of the blood or a substantially cylindrical blood suction port protruding upward, and the above-mentioned suction catheter 12 is connected to the patient-side port 56. The patient-side port 56 penetrates the upper bottom wall portion 48 or the annular wall portion 50 in the vertical direction, and communicates the bottle lid 16 inside and outside.

Further, the upper bottom wall portion 48 or the annular wall portion 50 is provided with an aspirator-side port 58 as a substantially cylindrical negative pressure acting port that projects upward and is separated from the patient-side port 56. The aspirator-side port 58 penetrates the upper bottom wall portion 48 or the annular wall portion 50 in the vertical direction, and communicates the bottle lid 16 inside and outside. In the present practical embodiment, the patient-side port 56 and the aspirator-side port 58 are provided at positions off the center of the upper bottom wall portion 48 in a plan view. In particular, in the present practical embodiment, the patient-side port 56 and the aspirator-side port 58 are provided on opposite sides of the center of the upper bottom wall portion 48, and face each other in the diametrical direction (left and right direction in FIG. 2). In the upper bottom wall portion 48 or the annular wall portion 50, a through hole 60 penetrating in the vertical direction is provided on the outer peripheral side of the aspirator-side port 58. The through hole 60 always communicates with the inside and outside of the bottle lid 16. However, since the through hole 60 is a very small hole so that it is not substantially affected to the suction bottle 10 even when a negative pressure pump 104 described later is operated and the internal pressure of the suction bottle 10 is negative. Further, by stopping the negative pressure pump 104 after the blood clot suction operation is completed, the pressure inside the suction bottle 10 can be gradually brought closer to the atmospheric pressure through the through hole 60, and the inside of the suction bottle 10 becomes negative pressure. As a result, it can be avoided that the bottle lid 16 becomes difficult to remove from the bottle body 14.

The aspirator-side port 58 of the present practical embodiment has a double-cylinder structure in which the inside and outside are inserted into each other, and a female screw is provided on the inner peripheral surface of the tubular portion on the outer peripheral side, by which the aspirator-side members such as connectors are connected with a lock structure.

In the upper bottom wall portion 48 or the annular wall portion 50, an insertion cylinder portion 62 projecting downward is provided at a position corresponding to the aspirator-side port 58, and communicates with the aspirator-side port 58. Further, on the outer peripheral side of the insertion cylinder portion 62, a support cylinder portion 64 protruding downward from the upper bottom wall portion 48 or the annular wall portion 50 is provided. A plurality of support protrusions 66 are formed on the inner peripheral surface of the support cylinder portion 64 so as to be separated from each other in the circumferential direction.

As shown in FIG. 2, a filter 68 is attached to the support cylinder portion 64. The filter 68 has a substantially bottomed tubular shape that opens upward, and is extrapolated to the insertion cylinder portion 62 at the upper opening. The filter 58 is fixedly supported with the support protrusion 66 of the support cylinder portion 64 abutting on an outer peripheral surface of the filter 68. As a result, the negative pressure suction from the aspirator-side port 58 is applied to the inside of the bottle through the filter 68.

Further, the bottle lid 16 of the present practical embodiment is provided with a lid-side engaging portion 70 that engages with the bottle body 14 in the cylindrical portion 54. That is, at the lower end of the cylindrical portion 54, an engaging protrusion 72 corresponding to the gap 36 of the body-side engaging portion 32 is formed so as to project toward the inner peripheral side. Further, at the lower end of the cylindrical portion 54, a lid-side engaging projection 74 corresponding to the body-side engaging protrusion 40 of the body-side engaging portion 32 is formed so as to be separated from the engaging protrusion 72 in the circumferential direction.

As shown in FIG. 5, an annular reinforcing rib 76a and a plurality of linear reinforcing ribs 76b radially extending from the annular reinforcing rib 76a are provided on the lower surfaces of the upper bottom wall portion 48 and the annular wall portion 50. In addition, in order to improve the visibility, the reinforcing ribs 76a and 76b are not shown in FIG. 2.

In order to assemble the bottle body 14 provided with the sealing member 42 and the bottle lid 16 as described above, the gap 36 in the body-side engaging portion 32 and the engaging protrusion 72 in the lid side engaging portion 70 are aligned in the circumferential direction. In the aligned state, the opening of the bottle body 14 is covered with the bottle lid 16 from above. Then, after the engaging protrusion 72 has passed through the gap 36, the bottle lid 16 is rotated to the other side in the circumferential direction with respect to the bottle body 14, so that the engaging protrusion 72 and the dead end surface 38 are mutually connected. Along with the contact, the lid-side engaging projection 74 gets over the body-side engaging protrusion 40. As a result, a sense of moderation is given to the operation of attaching and detaching the bottle lid 16, and the relative rotation of the bottle body 14 and the bottle lid 16 in the detaching direction is given a resistance force over the protrusions. This makes it possible to prevent unintentional release of the bottle lid 16 from the bottle body 14.

In the assembled portion between the bottle body 14 and the bottle lid 16 assembled in this way, sealing by the sealing member 42 is realized. That is, the flange-shaped portion 52 of the bottle lid 16 is substantially in close contact with the upper end surface of the sealing member 42 fixedly attached to the bottle body 14. Preferably, the flange portion 44 of the sealing member 42 is compressed between the upper end of the cylindrical wall portion 22 of the bottle body 14 and the flange-shaped portion 52 in the vertical direction. Therefore, in the present practical embodiment, the assembling portion between the bottle body 14 and the bottle lid 16 is composed of the upper end portion of the cylindrical wall portion 22 and the flange-shaped portion 52. In particular, in the present practical embodiment, since the annular rib 23 is provided on the upper end surface of the cylindrical wall portion 22, the flange portion 44 is more reliably compressed, and the bottle body 14 and the bottle lid 16 by the sealing member 42 Sealability can be improved.

The area surrounded by the bottle body 14 and the bottle lid 16 is the internal space of the bottle housing 18, and the suction bottle 10 has the internal space of the upper region 78 and the lower region 80. A thrombus trapping member 82 that spreads in a divided manner is provided. The thrombus trapping member 82 is preferably an integrally molded product made of, for example, a hard synthetic resin, and is preferably formed of a transparent (including translucent) material. In the present practical embodiment, substantially the entire thrombus trapping member 82 is made of a transparent material.

Figure 6:
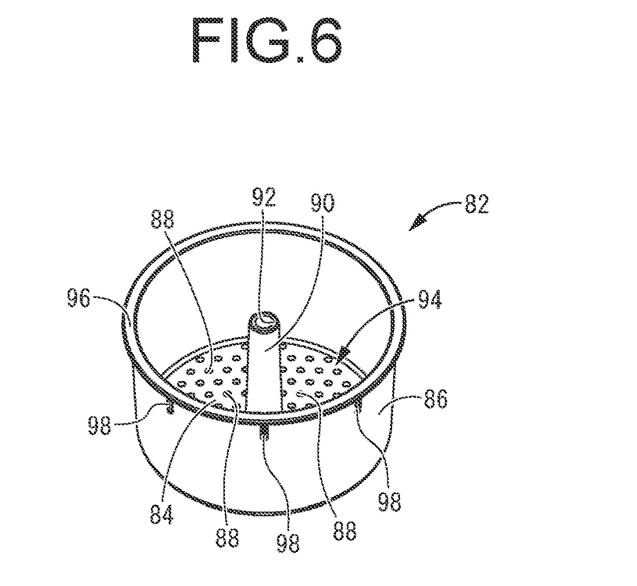
FIG. 6 is a perspective view of a thrombus trapping member of the suction bottle shown in FIG. 1.
Figure 7:
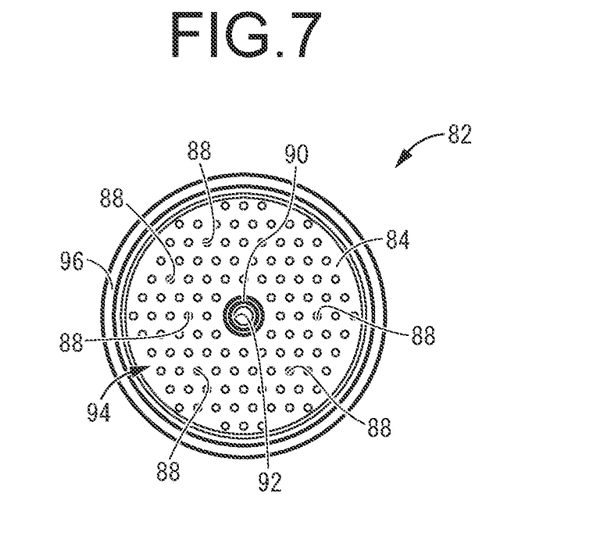
FIG. 7 is a plan view of the thrombus trapping member shown in FIG. 6.
Figure 8:
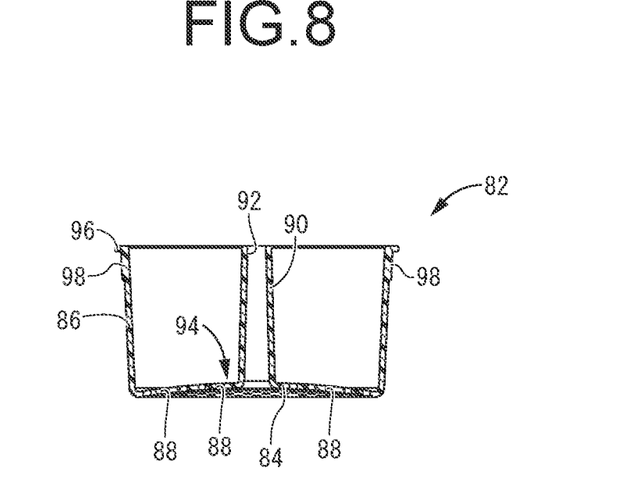
FIG. 8 is a vertical cross sectional view of the thrombus trapping member shown in FIG. 6.

As shown in FIGS. 6 to 8, the thrombus trapping member 82 of the present practical embodiment includes a plate-shaped portion 84 that extends substantially laterally and a peripheral vertical wall portion that rises upward from the outer peripheral portion of the plate-shaped portion 84. That is, in the present practical embodiment, the plate-shaped portion 84 has a substantially circular shape, and constitutes a portion that expands so as to partition the inner space of the bottle into an upper region 78 and a lower region 80. The plate-shaped portion 84 is formed as a peripheral vertical wall portion having a tubular shape, which is continuous over the entire circumference in the circumferential direction and has a certain vertical dimension. As a result, the thrombus trapping member 82 has a substantially cup-shaped or substantially bottomed cylindrical shape as a whole, and the upper region 78 and the lower region 80 are separated in the vertical direction by the plate-shaped portion 84. It is partitioned in the radial direction by the peripheral wall portion 86. As a result, with respect to the thrombus trapping member 82, the space above the plate-shaped portion 84 and on the inner peripheral side of the peripheral wall portion 86 is set as the upper region 78, and below the plate-shaped portion 84 and from the peripheral wall portion 86. The space on the outer peripheral side is defined as the lower region 80. In the present practical embodiment, the peripheral wall portion 86 is formed in a tapered tubular shape in which the diameter dimension gradually decreases downward.

Further, the plate-shaped portion 84 is provided with a plurality of circular through holes 88 penetrating in the vertical direction, and the upper region 78 and the lower region 80 inside the suction bottle 10 communicate with each other through the through holes 88. In the present practical embodiment, the through holes 88 are provided over substantially the entire plate-shaped portion 84. The number, shape, size (inner diameter dimension) and density (denseness) of the through holes 88 can be appropriately set according to the ease of capture, the ease of blood flow, etc. For example, through holes of a plurality of types and sizes may be adopted, or the densities may be partially different.

The thrombus trapping member 82 of the present practical embodiment includes a hollow tubular portion 90 projecting upward from the center of the plate-shaped portion 84, that is, into the upper region 78, and the plate-shaped portion 84 is formed to be annular in a plan view. The tubular portion 90 has no through holes or the like in the peripheral wall constituting the tubular portion 90, and is open only at both the upper and lower ends. That is, the upper region 78 and the lower region 80 inside the suction bottle 10 are communicated with each other not only by the through hole 88 but also by the hollow hole 92 of the tubular portion 90. As a result, the ventilation passage that allows air to flow between the upper region 78 and the lower region 80 is composed of a hollow hole 92 having a cross-sectional area larger than that of the through hole 88. Further, the opening position on the upper side of the tubular portion 90 is substantially the same as or higher than the upper end of the peripheral wall portion 86, and is at least higher than the through hole 88 provided in the plate-shaped portion 84 and is a hollow hole facing upward. 92 is open.

The tubular portion 90 of the present practical embodiment has a substantially cylindrical shape and a tapered tubular shape in which the diameter dimension gradually decreases upward. In addition to the fact that the peripheral wall portion 86 also has a tapered cylindrical shape, the space between the peripheral wall portion 86 and the tubular portion 90 in the radial direction gradually increases in the radial width dimension upward. However, the shape of the tubular portion 90 is not limited to the tubular or cylindrical shape. As will be described later, when the knob portion is formed by the tubular portion 90, the tubular portion 90 can be easily picked, so it may have a polygonal cylinder shape such as a triangular cylinder shape or a square cylinder shape. It suffices if a ventilation passage that allows air to flow between the upper region 78 and the lower region 80 is formed through the tubular portion 90. For example, the upper end of the tubular portion 90 is closed and opens laterally. Alternatively, the lower end of the tubular portion 90 may project downward from the plate-shaped portion 84 to open.

Further, as will be described later, the thrombus trapping member 82 is arranged substantially coaxially with the bottle body 14, and the tubular portion 90 protruding upward from the center of the plate-shaped portion 84 is the bottle lid 16 in a plan view. It is located approximately in the center of the upper bottom wall portion 48 in the above. That is, in the present practical embodiment, the patient-side port 56 and the aspirator-side port 58 and the tubular portion 90 are provided so as not to overlap (in the vertical direction) in a plan view, and the patient-side port 56 and the aspirator-side port 58 are located between the peripheral wall portion 86 and the tubular portion 90 in the radial direction.

Furthermore, the tubular portion 90 has a vertical dimension substantially equal to that of the peripheral wall portion 86. As a result, the user inserts his/her finger into the bottle body 14 and the thrombus trapping member 82, in the single item state before assembly or in the state where the bottle lid 16 is removed from the suction bottle 10, and can hold a tip end of the tubular portion 90. In the present practical embodiment, the knob portion of the thrombus trapping member 82 projecting to the upper region 78 is formed by the tubular portion 90. However, the tubular portion 90 may have a vertical dimension smaller than that of the peripheral wall portion 86, or may have a large vertical dimension, and even if the outer peripheral surface is roughened so that the fingers do not slip easily.

In particular, in the present practical embodiment, the patient-side port 56 extends slightly downward from the upper bottom wall portion 48 so that the patient-side port 56 and the tubular portion 90 do not overlap each other in the lateral direction. The insertion cylinder portion 62 also has a protruding dimension that does not reach the tubular portion 90, but the support cylinder portion 64 overlaps the tubular portion 90 in the lateral direction, and the thrombus trapping member 82 is assembled. In the attached state, the protruding tip of the support cylinder portion 64 is inserted between the peripheral wall portion 86 and the tubular portion 90 in the radial direction. However, the vertical dimensions of the patient-side port 56, the insertion cylinder portion 62, and the support cylinder portion 64 are not limited. For example, the patient-side port and the insertion cylinder portion overlap with the tubular portion in the lateral direction.

Further, the annular plate-shaped portion 84 is provided with an inclined portion 94 that is inclined with respect to the horizontal direction (substantially lateral direction), and in the present practical embodiment, substantially the entire plate-shaped portion 84 is inclined portion 94. In particular, in the present practical embodiment, both the upper surface and the lower surface of the plate-shaped portion 84 are gradually inclined downward from the inner peripheral side to the outer peripheral side, and the lower end of the tubular portion 90 is located above with respect to the lower end of the peripheral wall portion 86.

Furthermore, the upper opening portion of the peripheral wall portion 86 is provided with an annular outer peripheral protrusion 96 protruding toward the outer peripheral side. The outer peripheral protrusion 96 is formed with a certain radial width dimension. Further, the outer diameter dimension at the upper end portion of the peripheral wall portion 86 is substantially equal to or slightly larger than the inner diameter dimension of the main body portion of the sealing member 42, and the outer peripheral protrusion 96 is placed on the support surface 46 of the sealing member 42. As a result, the thrombus trapping member 82 is supported on the sealing member 42 substantially coaxially with the sealing member 42 and the bottle body 14. That is, the thrombus trapping member 82 can be supported by the bottle body 14 via the sealing member 42 at the upper opening portion of the peripheral wall portion 86.

When the thrombus trapping member 82 is supported by the sealing member 42 (bottle body 14), it is preferable that the main body portion of the sealing member 42 is in the radial direction between the cylindrical wall portion 22 of the bottle body 14 and the peripheral wall portion 86 of the thrombus trapping member 82, and compressed therebetween, thereby providing a seal between the bottle body 14 and the thrombus trapping member 82. In particular, in the present practical embodiment, a fitting protrusion 98 projecting to the outer peripheral side is formed on the outer peripheral surface of the upper end portion of the peripheral wall portion 86. As a result, at the forming position of the fitting protrusion 98, the main body portion of the sealing member 42 is more compressed in the radial direction, so that the sealability between the bottle body 14 and the thrombus trapping member 82 can be improved.

The support of the thrombus trapping member 82 by the sealing member 42 (bottle body 14) as described above is achieved at a portion located more inner side than the assembly portion between the bottle body 14 and the bottle lid 16 (the upper end of the cylindrical wall portion 22 and the flange-shaped portion 52). Therefore, the sealing of the bottle body 14 and the bottle lid 16 by the sealing member 42 is performed regardless of the presence or absence of the thrombus trapping member 82, that is, in the state in which the thrombus trapping member 82 is taken out from the suction bottle 10.

Figure 9:
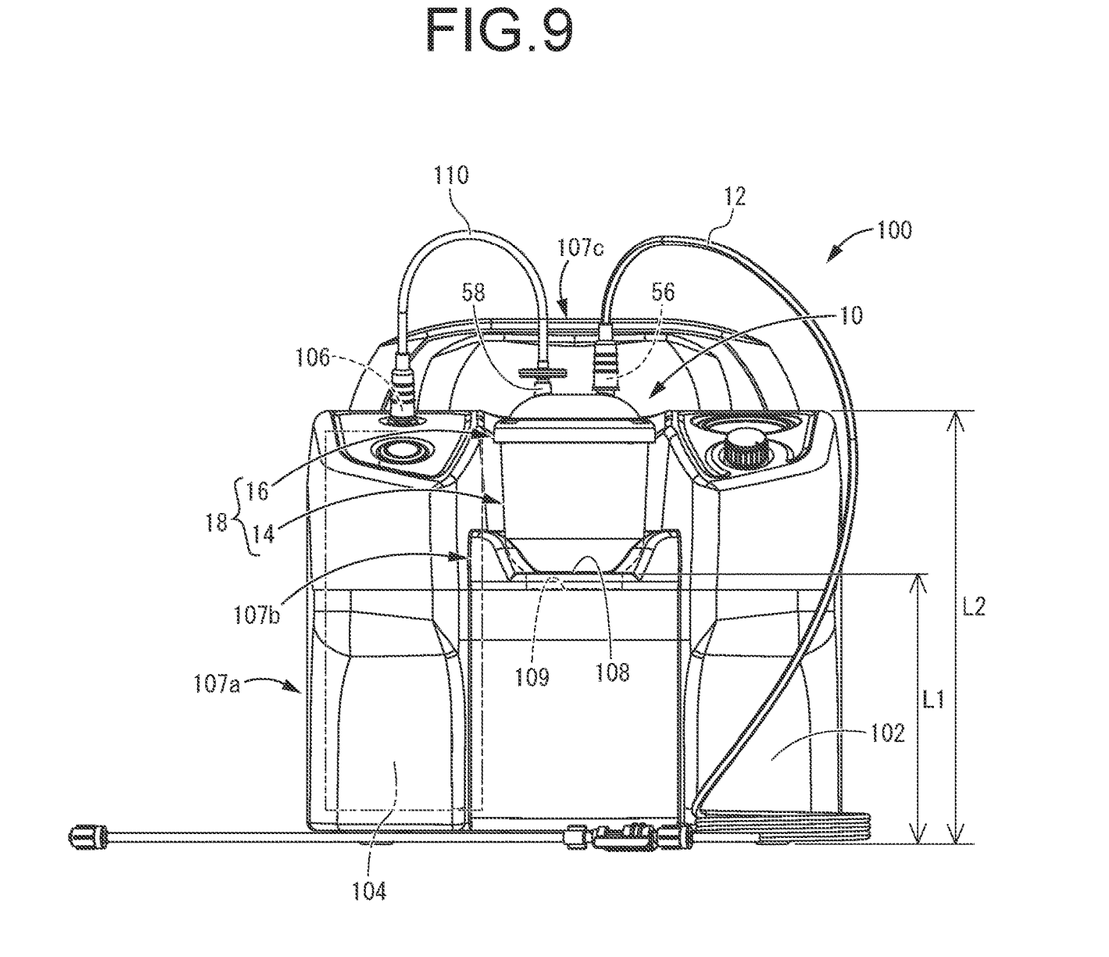
FIG. 9 is a front elevational view of a specific example of a thrombus aspirator to which the suction bottle shown in FIG. 1 is assembled.

The suction bottle 10 having the above structure is used by being detachably attached to the thrombus aspirator 100. Although a specific example of the thrombus aspirator 100 is shown in FIG. 9, the thrombus aspirator to which the suction bottle 10 is assembled is not limited to the one shown in FIG. 9.

The thrombus aspirator main body 102 of the thrombus aspirator 100 of the present practical embodiment includes a negative pressure pump 104 inside, and a negative pressure port 106 communicated with the negative pressure pump 104 projects to the outside of the thrombus aspirator main body 102. Further, the thrombus aspirator main body 102 may be provided with a power source for operating the negative pressure pump 104 and a pressure adjusting knob for adjusting the magnitude of the negative pressure.

Further, the thrombus aspirator main body 102 includes a housing 107a that can be divided into upper and lower parts. A seating portion 107b for mounting the suction bottle 10 is formed in the center of the housing 107a in the width direction, and the seating portion 107b is provided with a substantially circular mounting hole 108 that opens upward. Further, although the handle 107c is additionally provided on the upper portion of the housing 107a, the arrangement position of the handle 107c is not limited. In the present practical embodiment, for example, the lower part of the bottle body 14 is accommodated in the mounting hole 108, and the upper part of the bottle body 14 and the bottle lid 16 project from the mounting hole 108. As a result, the suction bottle 10 can be detachably assembled to the thrombus aspirator main body 102. In particular, in the present practical embodiment, the arrangement region of the thrombus trapping member 82 is not covered by the thrombus aspirator main body 102 at least on the front side of the thrombus aspirator main body 102 when the suction bottle 10 is attached, as will be described later. It can be avoided that the visibility of the thrombus trapped on the thrombus trapping member 82 is lowered.

The bottom of the mounting hole 108 is provided with a circular fitting hole 109 corresponding to the leg portion 24 provided at the bottom of the bottle body 14, and the leg portion 24 is fitted into the fitting hole 109. The suction bottle 10 can be prevented from rattling with respect to the thrombus aspirator main body 102. As a result, in the present practical embodiment, the holding portion for holding the suction bottle 10 is configured to include the fitting hole 109. Further, in the present practical embodiment, since the leg portion 24 is provided with the short projecting piece 28b that can be flexed and deformed and the fitting protrusion 30 on the outer peripheral surface of the short projecting piece 28b, the short projecting piece 28b is flexed and deformed. As a result, the manufacturing error between the fitting hole 109 and the leg portion 24 is absorbed, and the fitting protrusion 30 comes into contact with the inner peripheral surface of the fitting hole 109, so that the rattling of the suction bottle 10 can be further prevented. Further, the fitting protrusion 30 of the short projecting piece 28b is partially in contact with the fitting hole 109 in the circumferential direction instead of the entire outer peripheral surface of the leg portion 24, so that the external force required for detachment of the suction bottle 10 from the thrombus aspirator main body 102 can be suppressed to a small size. Thus, the possibility that blood, thrombus, etc. in the suction bottle 10 may be scattered due to an impact when the suction bottle 10 is removed can be reduced.

In particular, in the present practical embodiment, the height position at the opening of the fitting hole 109, that is, the height dimension L1 from the floor surface to the deepest part inside the suction bottle 10 is set at the height dimension (vertical dimension) of the thrombosis aspirator main body 102. Namely, it is set at a height of ½ or more in the height dimension L2 of the housing 107a excluding the handle 107c provided separately. That is, by fitting the leg portion 24 into the fitting hole 109, for example, even when the upper half or more of the suction bottle 10 is projected from the seating portion 107b of the thrombus aspirator main body 102, the suction bottle 10 is sucked by the thrombus. It is possible to stably hold the suction bottle 10 with respect to the vessel body 102, and by setting the support position of the suction bottle 10 high, the thrombus trapped on the thrombus trapping member 82 and the bottle body 14 are accommodated. The visibility of blood can be further improved. The attached suction bottle 10 is surrounded by the housing 107a of the thrombus aspirator main body 102 in a region having a predetermined length in the circumferential direction from the rear to the left and right sides, so that occurrence of careless contact with the suction bottle 10 or the like is prevented.

Then, a negative pressure tube 110 is removably connected to the negative pressure port 106 of the thrombus aspirator main body 102. Further, the end of the negative pressure tube 110 on the side opposite to the side connected to the negative pressure port 106 is connected to the aspirator-side port 58 of the suction bottle 10 and communicates with the inside of the suction bottle 10. As a result, the negative pressure pump 104 and the suction bottle 10 can communicate with each other. The negative pressure tube 110 may be connected to the aspirator-side port 58 via an appropriate filter or the like, if necessary, or such a filter may not be provided. Further, the negative pressure tube 110 and the aspirator-side port 58 may be non-removable, and the suction bottle 10 may be configured to include the negative pressure tube 110. However, the negative pressure port 106 and the negative pressure tube 110 may be non-removable, and the negative pressure tube 110 and the aspirator-side port 58 may be removable, or the negative pressure tube 110 may be removable with respect to both of the negative pressure port 106 and the aspirator-side port 58.

When aspirating a patient's thrombus using such a suction bottle 10 and a thrombus aspirator 100, first, the suction bottle 10 is assembled into the mounting hole 108 of the thrombus aspirator main body 102, and the negative pressure port 106 and the aspirator are connect to the negative pressure tube 110 Further, the suction catheter 12 is connected to the patient-side port 56. As a result, the negative pressure tube 110 and the suction catheter 12 communicate with each other through the inside of the suction bottle 10.

In the present practical embodiment, both the patient-side port 56 and the aspirator-side port 58 are provided upward in the bottle lid 16. Thus, the width dimension of the bottle body 14 can be reduced as compared with the case where the aspirator-side port protrudes laterally from the lower region of the bottle body. In particular, in the present practical embodiment, the patient-side port 56 and the aspirator-side port 58 are provided at positions facing each other in the radial direction. This makes it possible to prevent that the suction catheter 12 extending from both ports 56 and 58 and the negative pressure tube 110 are entangled, and that the suction catheter 12 and the negative pressure tube 110 reduces visibility of the thrombus trapped on the thrombus trapping member 82 by the suction catheter 12 and the negative pressure tube 110.

Then, the suction catheter 12 is inserted into the patient, and the suction port of the suction catheter 12 is delivered to the vicinity of the occlusion position by the thrombus. After that, by turning on the power of the thrombus aspirator 100 and operating the negative pressure pump 104, a suction pressure is applied to the suction catheter 12 through the inside of the negative pressure tube 110 and the suction bottle 10, and the thrombus near the occlusion position is sucked together with the blood. The blood sucked together with the thrombus is allowed to flow into the upper region 78 of the suction bottle 10 through the suction catheter 12 and the patient-side port 56. That is, in the present practical embodiment, the patient-side port 56 is the inflow port of blood in the upper region 78, and the blood flowing down from the patient-side port 56 is made to flow in a radial space between the peripheral wall portion 86 and the tubular portion 90 in the upper region 78.

Further, the blood flowing into the upper region 78 is guided to the upper surface of the thrombus trapping member 82. Then, a thrombus having a size larger than that of the through holes 88 of the thrombus trapping member 82 is filtered by the thrombus trapping member 82, and blood that does not contain the thrombus or contains a thrombus that is smaller than the through holes 88 is discharged through the through holes 88, and flow down to the side region 80.

The negative pressure pump 104 sets the inside of the suction bottle 10 to an appropriate negative pressure. For example, the blood flowing into the suction bottle 10 may not be sucked into the thrombus aspirator 100 side through the aspirator-side port 58. Instead, the flow from the patient-side port 56 to the upper region 78 and the flow from the upper region 78 to the lower region 80 through the through hole 88 can be stably achieved, for example, by the action of gravity. However, even if blood is sucked into the aspirator-side port 58, by means of the filter 68 provided inside the aspirator-side port 58 and the filter appropriately provided outside the aspirator-side port 58, an intrusion of thrombus into the thrombus aspirator 100 can be effectively prevented.

When it is confirmed that the thrombus is captured by the thrombus trapping member 82 and the blood flow is restored, the suction operation is terminated. After that, the bottle lid 16 and the thrombus trapping member 82 are removed from the bottle body 14, the thrombus is collected from the thrombus trapping member 82 as needed, and the blood remaining in the bottle body 14 is discarded. At that time, by covering the bottle body 14 again with the bottle lid 16, the bottle housing 18 having blood inside can be easily carried.

The suction bottle 10 of the present practical embodiment having the above structure is provided with a thrombus trapping member 82, and by allowing blood containing the thrombus to flow down to the upper region 78, a thrombus having a size larger than the through holes 88 can catch the thrombus. While being trapped on the thrombus trapping member 82, blood containing a thrombus smaller than the through holes 88 is allowed to flow down into the lower region 80. Thereby, by checking the thrombus trapping member 82, it can be easily grasped whether or not the thrombus has been recovered. In particular, in the present practical embodiment, since substantially the entire bottle housing 18 and the thrombus trapping member 82 are made of a transparent material, it is possible to easily visually recognize that the thrombus has been collected by the thrombus trapping member 82 from the outside. Further, the thrombus can be easily separated from the sucked blood by the thrombus trapping member 82, and for example, the thrombus can be collected from the thrombus trapping member 82 and the thrombus can be precisely inspected.

Further, since the upper region 78 and the lower region 80 are communicated with each other by a ventilation passage (hollow hole 92 of the tubular portion 90) other than the through hole 88, the flow of blood through the through hole 88 can be stably realized, while preventing that the through hole 88 is blocked by blood sticking to the lower surface of the plate-shaped portion 84 due to surface tension or the like. In particular, in the present practical embodiment, the hollow hole 92 is provided at a position avoiding the blood inflow port (patient-side port 56). This makes it possible to prevent the blood flowing through the inflow port 56 from flowing directly down into the region 80 through the hollow hole 91 (ventilation passage).

Further, in the present practical embodiment, since the tubular portion 90 constituting the ventilation passage 92 is provided in the center of the plate-shaped portion 84, the area of the annular region in which the through hole 88 is provided in the plate-shaped portion 84, can be widely secured. In particular, in the present practical embodiment, the tubular portion 90 constitutes a knob portion, and the thrombus trapping member 82 can be easily removed by pinching the knob portion. As a result, the work of collecting the thrombus from the thrombus trapping member 82 can be easily performed, and it is possible to make it easier to perform a precise examination of the thrombus. In addition to that, since the tubular portion 90 constituting the ventilation passage 92 can be skillfully used to form the knob portion, the structure can be simplified and made more compact than, for example, when the knob portion is separately formed.

Furthermore, the thrombus trapping member 82 has a peripheral vertical wall portion (peripheral wall portion 86). This makes it possible to prevent that the blood flowing into the thrombus trapping member 82 flows down from the outer peripheral side of the plate-shaped portion 84 to the lower region 80. In particular, in the present practical embodiment, since the peripheral vertical wall portion is the peripheral wall portion 86 over the entire circumference, the flow of blood to the lower region 80 not through the through hole 88 can be further prevented.

Further, since the thrombus trapping member 82 is supported on the sealing member 42 by the outer peripheral protrusion 96 provided at the upper end of the peripheral wall portion 86, the peripheral wall portion 86 and the outer peripheral protrusion 96 are provided over the entire circumference. Therefore, the support stability of the thrombus trapping member 82 can also be improved. In particular, in the present practical embodiment, the thrombus trapping member 82 has a cup shape, and the outer peripheral protrusion 96 over the entire circumference is provided by skillfully utilizing the peripheral wall portion 86 provided over the entire circumference. Therefore, it is not necessary to separately provide a support portion for the sealing member 42, which not only prevents blood from flowing down to the lower region 80, but also achieves simplification and compactness of the structure and improvement of support stability.

Further, in the thrombus trapping member 82, since the upper surface of the plate-shaped portion 84 is inclined downward as it is separated from the tubular portion 90 (toward the outer peripheral side), the blood on the thrombus trapping member 82 is directed to the outer peripheral side. Can be fluidized. As a result, in the thrombus trapping member 82, the amount of blood flowing down to the lower region 80 through the through hole 88 near the tubular portion 90 can be reduced. Further, since the lower surface of the plate-shaped portion 84 is also inclined downward as it is separated from the tubular portion 90 (toward the outer peripheral side), the blood flowing down through the through hole 88 can flow to the outer peripheral side. The inclination of at least one of the upper and lower surfaces of the plate-shaped portion 84 can reduce the possibility that blood that has spilled over to the lower surface of the thrombus trapping member 82 through the through hole 88 blocks the lower opening of the tubular portion 90.

Furthermore, the assembling portion between the bottle body 14 and the bottle lid 16 is sealed by the sealing member 42 regardless of the presence or absence of the thrombus trapping member 82. Therefore, upon disposing the blood during or after sucking the thrombus, for example, it is possible to prevent blood from leaking from the bottle housing 18.

Although the practical embodiments of the present invention have been described above, the present invention is not limitedly interpreted by the specific description in the practical embodiments, and it can be carried out in the form of adding various changes, modifications, improvements, etc., which are made based on the knowledge of those skilled in the art.

For example, the suction bottle 10 in the practical embodiment has the technical effect of (1) being able to easily determine whether or not a thrombus has been captured, and (2) being able to easily separate the thrombus from the collected blood. Although a plurality of effects such as technical effects have been exhibited, only one of these technical effects may be exhibited. That is, in the above practical embodiment, substantially the entire bottle housing 18 and the thrombus trapping member 82 are transparent, whereby the technical effect of the above (1) can be advantageously exhibited. A transparent window portion may be provided in a part of the thrombus trapping member so that the thrombus on the thrombus trapping member can be visually recognized through the window portion. However, for example, if the technical effect of (2) above is exhibited, it is not essential that the thrombus be visually recognized from the outside. It may be possible to check if there is a thrombus on the thrombus trapping member, by removing the lid from the bottle body, after a certain amount of time has passed since the start of suction.

Further, in the above-described practical embodiment, the thrombus trapping member 82 has a substantially cup-shaped shape, but the present invention is not limited to this embodiment. That is, the thrombus trapping member may be provided so as to divide the inside of the bottle into an upper region and a lower region. For example, the outer peripheral edge portion of the plate-shaped thrombus trapping member spreading in the lateral direction may be fixed on the inner peripheral surface of the bottle body. In that case, it can be grasped that the surrounding vertical wall portion (peripheral wall portion) is composed of the bottle body.

Further, in the above-described practical embodiment, in the thrombus trapping member 82 formed in a substantially cup shape by a hard synthetic resin, a through hole 88 is provided in a plate-shaped portion 84 serving as a bottom wall portion. A tubular peripheral wall portion may be formed, and a mesh-shaped plate-shaped portion may be provided so as to cover the lower opening thereof, and a through hole may be formed by a gap between the meshes. In that case, the material of the plate-shaped portion is not limited, and for example, a metal plate-shaped portion is adopted. Therefore, in the above-described practical embodiment, the thrombus trapping member 82 is substantially cup-shaped and the plate-shaped portion 84 and the peripheral wall portion 86 are integrally formed. However, the plate-shaped portion and the surrounding vertical wall portion (peripheral wall portion) are separately formed, and post-fixed. Further, in the above practical embodiment, substantially the entire thrombus trapping member 82 is formed of a transparent material, but for example, the plate-shaped portion may be white, and after the plate-shaped portion and the peripheral wall portion are integrally formed. The plate-shaped portion may be colored white, or the plate-shaped portion formed of a white material and the peripheral wall portion formed of a transparent material may be formed separately and post-fixed. This can improve the visibility of the thrombus trapped in the plate-shaped portion. However, the through hole may be provided in the surrounding vertical wall portion (peripheral wall portion) in place of or in addition to the plate-shaped portion in the thrombus trapping member. That is, for the thrombus trapping member, for example, only the peripheral vertical wall portion (peripheral wall portion) may be mesh-shaped, or the entire thrombus trapping member may be mesh-shaped without providing a through hole in the plate-shaped portion.

Furthermore, in the above-described practical embodiment, the knob portion is formed by the tubular portion 90 constituting the ventilation passage (hollow hole 92), but the knob portion and the ventilation passage (cylindrical portion) are formed as separate bodies. For example, the knob portion may protrude from the plate-shaped portion or the surrounding vertical wall portion. However, in the present invention, the knob is not essential.

Further, the ventilation passage is not limited to that described in the above practical embodiment. For example, the thrombus trapping member may have a shape in which a part of a circular outer peripheral portion is cut out in a plan view, and a ventilation passage may be formed by a space between the thrombus trapping member and the bottle body. Further, among the through holes formed in the plate-shaped portion, the through holes through which blood does not flow may be used as a ventilation passage, and when the through holes are provided in the surrounding vertical wall portion (peripheral wall portion), the through hole may be used as a ventilation passage. Although some modes of the ventilation passages have been illustrated as described above, these may be adopted in combination with each other, or a plurality of ventilation passages may be provided.

Further, in the above-described practical embodiment, substantially the entire plate-shaped portion 84 is an inclined portion 94 that inclines downward as it is separated from the ventilation passage, i.e., the hollow hole 92 (tubular portion 90), but the present invention is not limited to this embodiment. For example, an inclination as in the above practical embodiment may be provided in a part of the plate-shaped portion, or the plate-shaped portion may be inclined with respect to the horizontal direction throughout, and one of the radial directions to the other may be provided. It may be gradually inclined downward toward. Further, in the above-described practical embodiment, in the inclined portion 94, both the upper and lower surfaces of the plate-shaped portion 84 are inclined, but only one of the surfaces may be inclined. However, in the present invention, the inclined portion in the plate-shaped portion is not essential.

In the above practical embodiment, the aspirator-side port 58 to which the negative pressure tube 110 is connected is provided on the bottle lid 16, but the arrangement position of the aspirator-side port is not limited. For example, it is possible to provide the aspirator-side port in the bottle body constituting the lower region. In this case, it is not necessary to provide a ventilation passage for flowing the air in the lower region. It is preferable to adopt a configuration in which the aspirator-side port is not blocked by blood.

Further, a sealing member that seals between the bottle body and the bottle lid is not essential. In the above practical embodiment, the thrombus trapping member 82 is supported on the sealing member 42, but when the sealing member is not provided, the thrombus trapping member may be directly assembled to the bottle body. That is, the outer peripheral protrusion of the thrombus trapping member is supported on the upper end surface of the cylindrical wall portion of the bottle body, and the outer peripheral protrusion of the thrombus trapping member may be sandwiched between the upper end surface of the cylindrical wall portion and the flange portion of the bottle lid. Further, even when the sealing member is provided, it may or may not be fixed to the bottle lid instead of the bottle body.

Furthermore, in the practical embodiment, the thrombus trapping member 82 is supported on the sealing member 42, but the means for arranging the thrombus trapping member inside the bottle is not limited to that described in the practical embodiment. That is, for example, a tubular portion protruding upward from the thrombus trapping member is provided, and the tubular portion is extrapolated to the filter 68 or the support cylinder portion 64 in a substantially press-fitted state, whereby the thrombus trapping member is bottled. It may be fixed so as to be suspended from the lid, or the thrombus trapping member may be supported on the bottle housing in a non-fixed state.

Figure 10:
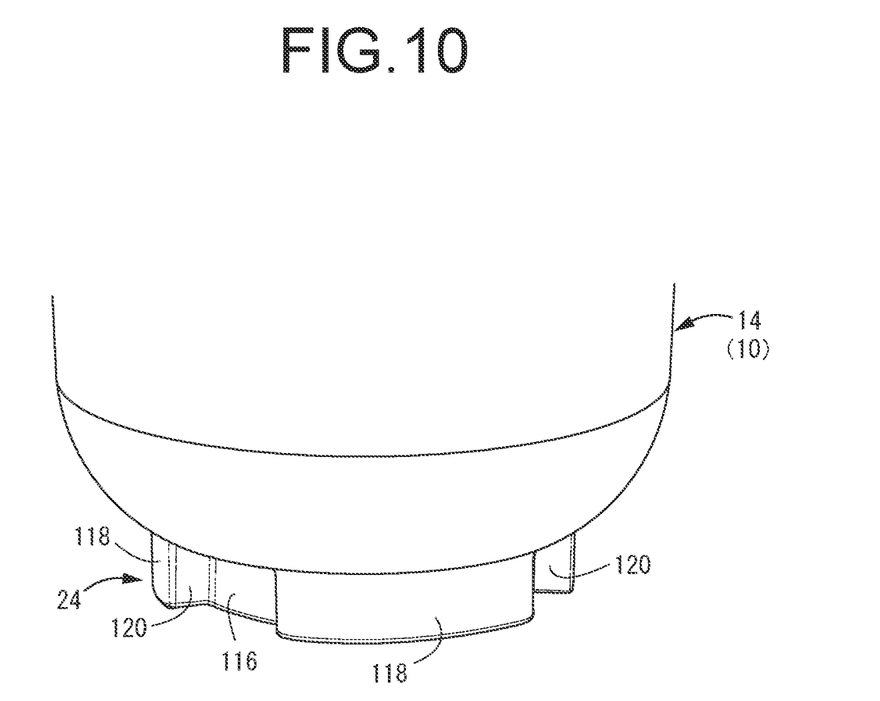
FIG. 10 is a perspective view showing an example of a modification of a leg part provided at a lower part of the suction bottle.

Further, the bottle body 14 may be positioned on the thrombus aspirator main body 102 and held in a mounted state, and the fitting structure of the lower part of the bottle body 14 to the thrombus aspirator main body 102 is not essential. Even when the leg portion 24 fitted to the thrombus aspirator main body 102 is adopted, the specific shape and structure of the leg portion 24 are not limited. For example, in place of or in addition to the above-mentioned fitting protrusions 30 that continuously extend the outer peripheral surface of the leg portion 24 in the vertical direction, an appropriate number of protrusions that partially protrude may be adopted, or the leg portion 24 having an outer peripheral surface provided with irregularities may be employed so as to be partially fitted. Further, as shown in FIG. 10 as an example of another embodiment, the cylindrical legs 24 formed continuously over the entire circumference in the circumferential direction is arranged to have different diametrical dimensions at different circumferential portions. This makes it possible to have small diameter portions 116 and large-diameter portions 118, which alternately and continuously in the circumferential direction via the stepped portions 120. The step portion 120 may have a curved shape without a break point that smoothly connects each small diameter portion 116 and each large diameter portion 118, and a region including one small diameter portion 116 and the step portions 120 and 120 on both sides has a shape of dent which draw a gentle curve as a whole. The large diameter portions 118 are partially fitted and held in contact with the inner peripheral surface of the circular fitting hole 109 of the thrombus aspirator main body 102 in the circumferential direction of the leg portion 24. Therefore, it is possible to suppress the fitting force and facilitate the attachment/detachment of the bottle body 14 as compared with the case where the entire circumference of the bottle is fitted into the fitting hole 109 in a contact state. It is also possible to adjust the fitting force to the fitting hole 109 by forming a fitting protrusion on the outer peripheral surface of the large diameter portion 118, if necessary. Furthermore, the thickness dimension of the leg portion 24 is partially different in the circumferential direction, for example, the thickness dimension of the portion to be fitted in contact with the fitting hole 109 of the thrombus aspirator main body 102 is reduced so as to reduce the deformation rigidity. This makes it possible to adjust the fitting force and facilitate the attachment/detachment operation of the bottle body 14. In addition, in order to facilitate fitting into the fitting hole 109, the lower end portion of the outer peripheral surface of the leg portion 24 may be reduced in diameter downward to provide a tapered guide surface.

KEYS TO SYMBOLS

10 Suction bottle (for thrombosis aspirator)
12 Suction catheter (suction tube)
14 Bottle body
16 Bottle lid
18 Bottle housing
20 Bottom wall portion
22 Cylindrical wall portion
23 annular rib
24 Leg portion
26 Notch
28 Projection pieces
28*a* Long projecting piece
28*b* Short projecting piece
30 Fitting protrusion
32 Body-side engaging portion
34 Engaging ridges
36 Gap
38 Dead end surface
40 Body-side engaging protrusion
42 Sealing member
44 flange portion
46 Support surface
48 Upper bottom wall portion
50 Annular wall portion
52 Flange-shaped part (assembling portion)
54 Cylindrical portion
56 Patient-side port (inflow port/blood suction port)
58 Aspirator-side port (negative pressure acting port)
60 Through hole
62 Insertion cylinder portion
64 Support cylinder portion
66 Support protrusion
68 Filter
70 Lid-side engaging portion
72 Engaging protrusion
74 Lid-side engaging projection
76*a* Annular reinforcing rib
76*b* Linear reinforcing rib
78 Upper region
80 Lower region
82 Thrombosis trapping member
84 Plate-shaped portion
86 Peripheral wall part (peripheral vertical wall part)
88 Through hole
90 Tubular portion (Knob portion)
92 Hollow hole (ventilation passage)
94 Inclined portion
96 Peripheral protrusion
98 Fitting protrusion
100 Thrombosis aspirator
102 Thrombosis aspirator main body
104 Negative pressure pump
106 Negative pressure port
107*a* Housing
107*b* Seating portion
107*c* Handle
108 Mounting hole
109 Fitting hole (holding portion)
110 Negative pressure tube
116 Small diameter portion
118 Large diameter portion
120 Step portion

The invention claimed is:
1. A suction bottle for a thrombus aspirator comprising:
a thrombus trapping member that spreads so as to divide an inside of the bottle into an upper region and a lower region;
a plurality of through holes formed in the thrombus trapping member so that blood guided to an upper surface of the thrombus trapping member flows down from the upper region to the lower region via the through holes; and
a ventilation passage that allows a flow of air between the upper region and the lower region inside the bottle, the ventilation passage being provided at a position avoiding an inflow port of the blood in the upper region, wherein
the thrombus trapping member includes: a plate-shaped portion extending between the upper region and the lower region; and a tubular portion with a hollow inside that projects upward from the plate-shaped portion, and the ventilation passage is formed by the hollow inside of the tubular portion; and
the tubular portion projects upward from a center of the plate-shaped portion while the plate-shaped portion spreads around a bottom end of the tubular portion.

2. The suction bottle according to claim 1, wherein the thrombus trapping member includes: a plate-shaped portion extending between the upper region and the lower region; and a peripheral vertical wall portion that rises upward at an outer peripheral portion of the plate-shaped portion.

3. The suction bottle according to claim 2, wherein the peripheral vertical wall portion is formed by a cylindrical peripheral wall portion so that the thrombus trapping member is formed into a cup shape as a whole, and the thrombus trapping member is supported with respect to a bottle body at the upper opening portion of the peripheral wall portion.

4. The suction bottle according to claim 1, wherein the thrombus trapping member is configured to be gripped by fingers by picking the tubular portion of the thrombus trapping member.

5. The suction bottle according to claim 1, wherein the thrombus trapping member includes a plate-shaped portion extending between the upper region and the lower region, and at least one of the upper surface and a lower surface of the plate-shaped portion has an inclined portion inclined with respect to a horizontal direction.

6. The suction bottle according to claim 1, further comprising: a bottle housing of a closed structure for accommodating the thrombus trapping member, the bottle housing having a bottle body that opens upward and a bottle lid that covers an opening of the bottle body, wherein the bottle lid includes: a blood suction port to which a suction tube for sucking the blood into the inside of the bottle is connected; and a negative pressure action port to which a negative pressure tube for applying a suction pressure to the suction tube via the inside of the bottle is connected, the blood suction port and the negative pressure action port being provided at different positions on the bottle lid.

7. The suction bottle according to claim 1, further comprising: a bottle housing of a closed structure for accommodating the thrombus trapping member, the bottle housing having a bottle body that opens upward and a bottle lid that covers an opening of the bottle body, wherein the thrombus trapping member is supported by a sealing member that seals an assembly portion between the bottle body and the bottle lid, and the sealing member realizes a sealing of the assembled portion between the bottle body and the bottle lid regardless of a presence or absence of the thrombus trapping member.

8. The suction bottle according to claim 1, wherein the thrombus trapping member is provided with a knob portion protruding to the upper region.

9. A thrombus aspirator comprising:
a thrombus aspirator main body provided with a negative pressure pump;
a suction bottle according to claim 1, the suction bottle being detachably assembled to the thrombus aspirator main body; and
a negative pressure tube communicated with an inside of the suction bottle, the negative pressure tube being detachably connected to a negative pressure port of the negative pressure pump.

10. The thrombus aspirator according to claim 9, wherein the thrombus aspirator main body includes a holding portion for holding the suction bottle in a state where a deepest portion of the inside of the suction bottle is located at a position at a height of ½ or more in a height direction of the thrombus aspirator main body.

11. The suction bottle according to claim 1, further comprising a vacuum port, wherein the ventilation passage is separate from the vacuum port.

12. A suction bottle for a thrombus aspirator comprising:
a thrombus trapping member that spreads so as to divide an inside of the bottle into an upper region and a lower region;
a plurality of through holes formed in the thrombus trapping member so that blood guided to an upper surface of the thrombus trapping member flows down from the upper region to the lower region via the through holes;
a bottle housing of a closed structure for accommodating the thrombus trapping member, the bottle housing having a bottle body that opens upward and a bottle lid that covers an opening of the bottle body; and
a sealing member that seals an assembly portion between the bottle body and the bottle lid, the sealing member being formed independently from the thrombus trapping member, wherein
the sealing member includes a flange portion in an outer peripheral side, the flange portion being configured to be compressed between the bottle body and the bottle lid, and a support surface in an inner peripheral side, the support surface being configured to support the thrombus trapping member without being compressed between the bottle body and the bottle lid,
a supported part of the thrombus trapping member is supported by the support surface of the sealing member so that the thrombus trapping member is assembled within the bottle body, and
the sealing member realizes a sealing of the assembled portion between the bottle body and the bottle lid regardless of a presence or absence of the thrombus trapping member.

* * * * *